United States Patent
Chen

(10) Patent No.: US 10,350,106 B2
(45) Date of Patent: Jul. 16, 2019

(54) WOMEN'S URINAL DEVICE

(71) Applicant: Ce Ren Chen, Brooklyn, NY (US)

(72) Inventor: Ce Ren Chen, Brooklyn, NY (US)

( * ) Notice: Subject to any disclaimer, the term of this patent is extended or adjusted under 35 U.S.C. 154(b) by 0 days.

(21) Appl. No.: 15/405,083

(22) Filed: Jan. 12, 2017

(65) Prior Publication Data

US 2019/0083297 A1 Mar. 21, 2019

(51) Int. Cl.
*A47K 11/12* (2006.01)
*A61F 5/455* (2006.01)

(52) U.S. Cl.
CPC ............ *A61F 5/4556* (2013.01); *A47K 11/12* (2013.01)

(58) Field of Classification Search
CPC ...................................................... A61G 9/006
USPC ................................................ 4/144.1–144.3
See application file for complete search history.

(56) References Cited

U.S. PATENT DOCUMENTS

| | | | | |
|---|---|---|---|---|
| 2,878,486 A * | 3/1959 | Bartlett | A61F 5/4556 | 4/144.4 |
| 4,681,573 A * | 7/1987 | McGovern | A61F 5/4556 | 4/144.3 |
| 4,683,598 A * | 8/1987 | Jones | E03D 1/003 | 4/144.1 |
| 5,065,459 A * | 11/1991 | Tjahaja | A61F 5/44 | 4/144.2 |
| 5,333,330 A * | 8/1994 | Murtagh | A47K 11/12 | 4/144.2 |
| 5,408,703 A * | 4/1995 | Cicio | A47K 11/12 | 4/144.2 |
| 5,742,948 A * | 4/1998 | Cicio | A47K 11/06 | 141/337 |
| 5,852,830 A * | 12/1998 | Horn | A47K 11/12 | 383/33 |
| 5,893,176 A * | 4/1999 | Magiera | A61F 5/4556 | 4/144.3 |
| 5,966,748 A * | 10/1999 | Young | A47K 11/12 | 4/144.4 |
| 6,199,220 B1 * | 3/2001 | Smith | A47K 11/045 | 4/144.2 |
| 6,434,757 B1 * | 8/2002 | Filsouf | A61F 5/4556 | 4/144.1 |
| 6,460,200 B1 * | 10/2002 | Mottale | A61F 5/4556 | 141/331 |
| D495,798 S * | 9/2004 | Gugliotta | A47K 11/12 | D24/122 |
| D527,101 S * | 8/2006 | Fernandez | A47K 11/12 | D24/122 |

(Continued)

*Primary Examiner* — Lori L Baker
(74) *Attorney, Agent, or Firm* — The Iwashko Law Firm, PLLC; Lev Ivan Gabriel Iwashko

(57) ABSTRACT

A women's urinal device that allows women to urinate while standing upright to conserve water and space required by conventional toilets or commodes. The women's urinal device is adapted to be held against a woman's vaginal area to receive urine excreted from a woman, the urine then is adapted to be excreted therethrough the interior of the generally conical-shaped funnel and therethrough an aperture formed on the bottom of the generally conical-shaped funnel, where the urine is adapted to be directed into a urinal. The women's urinal device is adapted to be dispensed from a funnel dispenser that is attached to the bathroom partition adjacent to the urinal to conveniently access the women's urinal device.

6 Claims, 2 Drawing Sheets

(56) References Cited

U.S. PATENT DOCUMENTS

| | | | | |
|---|---|---|---|---|
| D602,156 S | * | 10/2009 | Young | A47K 11/12 D24/122 |
| 7,682,347 B2 | * | 3/2010 | Parks | A61F 5/4556 206/210 |
| D650,902 S | * | 12/2011 | Lopez, Jr. | A47K 11/12 D24/122 |
| 8,146,179 B1 | * | 4/2012 | Duque | A61F 5/4556 4/144.1 |
| 8,337,477 B2 | * | 12/2012 | Parks | A61F 5/4556 604/329 |
| D703,811 S | * | 4/2014 | Ludert | A47K 11/12 D24/122 |
| D754,334 S | * | 4/2016 | Rudolph | A47K 11/12 D24/122 |
| D757,257 S | * | 5/2016 | Grossman | A47K 11/12 D24/122 |
| D760,383 S | * | 6/2016 | Delarosa | A47K 11/12 D24/122 |
| 9,744,068 B2 | * | 8/2017 | Hughes | A61F 5/451 |
| 2008/0034481 A1 | * | 2/2008 | Cheng | A47K 11/12 4/144.3 |
| 2010/0263113 A1 | * | 10/2010 | Shelton | A61F 5/453 4/144.2 |
| 2012/0210502 A1 | * | 8/2012 | Baham | A61F 5/4556 4/144.3 |
| 2013/0239311 A1 | * | 9/2013 | Valenti | A61F 5/4556 4/144.3 |

* cited by examiner

WOMEN'S URINAL DEVICE

BACKGROUND OF THE INVENTION

Field of the Invention

The present invention is a urinal device. More specifically, the present invention is a women's urinal device.

Description of the Related Art

Urinals have been in use for centuries. However, their use is limited to men only. Use of conventional toilets or commodes by women not only results in increased consumption of water, it can also prove to be troublesome in crowded places, such as theaters, shopping malls, clubs and other venues. As a result, females are required to spend more time standing in the bathroom queues, which may be frustrating for many.

What is needed is a women's urinal device that addresses and solves these problems.

SUMMARY OF THE INVENTION

The present invention is a urinal device. More specifically, the present invention is a women's urinal device.

The women's urinal device includes a generally conical-shaped funnel having a top, a bottom and an interior, the top of the generally conical-shaped funnel forms a pair of side wings that are adapted to be held against a woman's vaginal area to receive urine excreted from a woman, the urine then is adapted to be excreted therethrough the interior of the generally conical-shaped funnel and therethrough an aperture formed on the bottom of the generally conical-shaped funnel, where the urine is adapted to be directed into a urinal.

It is an object of the present invention to provide a women's urinal device that allow women to urinate while standing upright to conserve water and space required by conventional toilets or commodes.

It is an object of the present invention to provide a women's urinal device that is dispensed from a funnel dispenser that's mounted on one or more stall partitions or other suitable surface for easy to reach access.

It is an object of the present invention to provide a women's urinal device that is made from recyclable material to ensure sustainability.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention however the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
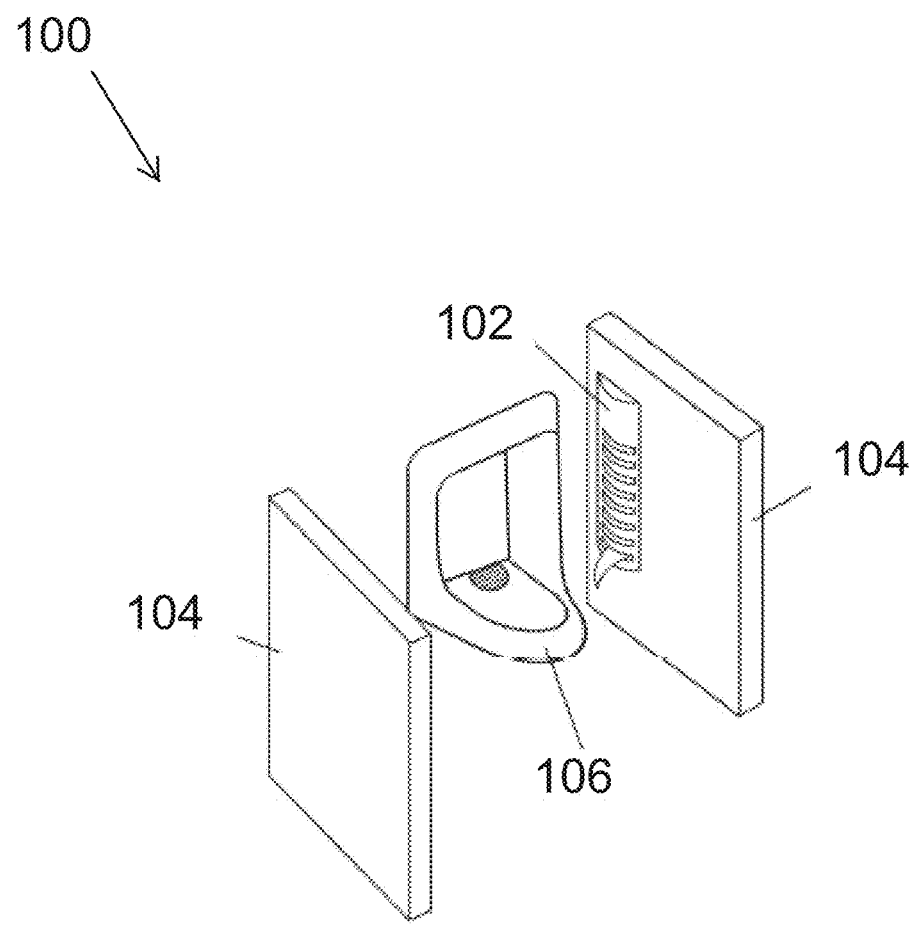
FIG. 1 illustrates an environmental front perspective view of a women's urinal device, in accordance with one embodiment of the present invention.

FIG. 1 illustrates an environmental front perspective view of a women's urinal device 100, in accordance with one embodiment of the present invention. The women's urinal device 100 may be adapted to be dispensed from a funnel dispenser 102 that may be attached to a bathroom partition 104 or other suitable surface adjacent to a urinal 106 to conveniently access the women's urinal device 100.

Figure 2:
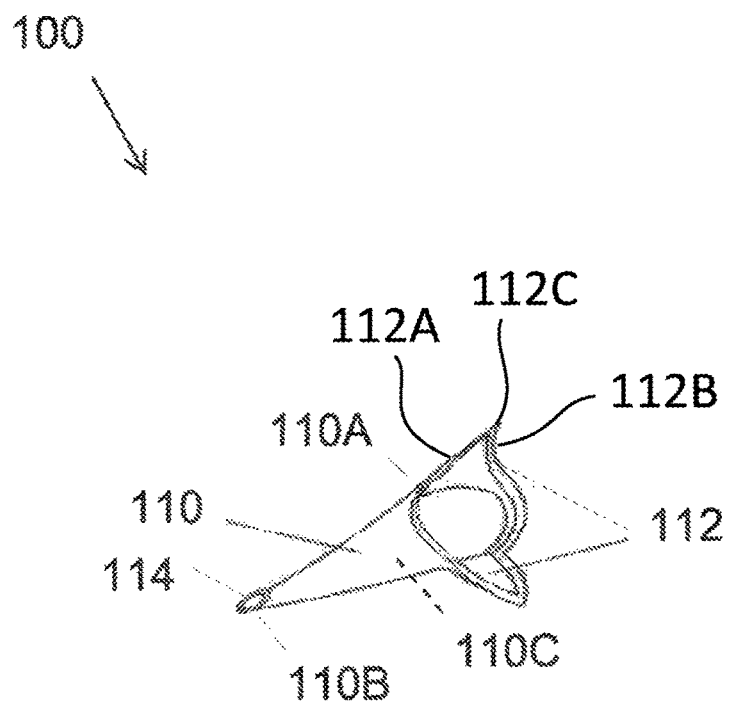
FIG. 2 illustrates a side perspective view of a women's urinal device, in accordance with one embodiment of the present invention.

FIG. 2 illustrates a side perspective view of a women's urinal device 100, in accordance with one embodiment of the present invention.

The women's urinal device 100 may include a generally conical-shaped funnel 110.

The generally conical-shaped funnel 110 may include a top 110A, a bottom 110B and an interior 110C. The top 110A of the generally conical-shaped funnel 110 forms a pair of side wings 112 that may be adapted to be held against a woman's vaginal area (not shown) to receive urine excreted from a woman. The urine then is adapted to be excreted therethrough the interior 110C of the generally conical-shaped funnel 110 and therethrough an aperture 114 formed on the bottom 110B of the generally conical-shaped funnel 110, where the urine is adapted to be directed into a urinal (FIG. 1, 106). This is in contrast to a woman sitting down trying to urinate into a toilet or commode, which is typically how women urinate. The pair of side wings 112 may be covered with removable and disposable tissue paper, that may be removed after each usage to promote hygiene and sanitation. The aperture 114 formed on the bottom 110B of the generally conical-shaped funnel 110 may be slanted to better direct any urine adapted to be excreted from the generally conical-shaped funnel 110. The generally conical-shaped funnel 110 may be made of recyclable and disposable waxed paper to promote recycling, conserve resources and promote sanitation. The waxed paper also provides a smooth waterproof surface to prevent urine from seeping through the generally conical-shaped funnel 110 and to allow for quick urine flow therethrough the generally conical-shaped funnel 110.

Each of the pair of side wings 112 may include a first convex curved portion 112A, a second convex curved portion 112B, and a converging point 112C.

The first convex curved portion 112A and the second curved portion 112B may each be connected at one end thereof to form an arcuate structure that forms the converging point 112C. The pair of side wings 112 may fit appropriately around the woman's groin area and may prevent excreted urine from dripping onto the woman's feet and also prevents the urine spraying upwards.

While the present invention has been related in terms of the foregoing embodiments those skilled in the art will recognize that the invention is not limited to the embodiments described. The present invention may be practiced with modification and alteration within the spirit and scope of the appended claims. Thus, the description is to be regarded as illustrative instead of restrictive on the present invention.

What is claimed is:

1. A women's urinal device comprising: a generally conical-shaped funnel having a top, a bottom and an interior, said device being dispensed from a funnel dispenser attachable to a bathroom partition adjacent to a urinal for convenient access to the women's urinal device, said generally conical-shaped funnel comprising: a pair of side wings disposed on a portion of a top edge of the generally conical-shaped funnel that are adapted to be held against a woman's vaginal area to receive urine excreted from a woman, each of the pair of side wings, comprising: a first convex curved portion on a top edge of said side wing, a second convex curved portion on a top edge of said side wing, and a converging point to connect the first convex curved portion and the second convex curved portion at one end opposite said curved portion, such that the pair of side wings prevents urine from at least one of dripping and spraying upwards; said side wings being covered with removable and disposable tissue paper where said paper is removed after each usage to promote clean hygiene and sanitation, said funnel being made from a recyclable material; and an aperture formed on the bottom of the generally conical-shaped funnel, where the urine is adapted to be directed through the interior of the generally conical-shaped funnel and into a urinal while a user is standing.

2. The women's urinal device according to claim 1, wherein the aperture formed on the bottom of the generally conical-shaped funnel is slanted to better direct urine adapted to be excreted from the generally conical-shaped funnel.

3. The women's urinal device according to claim 1, wherein the generally conical-shaped funnel is made of recyclable and disposable waxed paper to promote recycling and conserve resources.

4. The women's urinal device according to claim 1, wherein the generally conical-shaped funnel is made of recyclable and disposable waxed paper to promote sanitation.

5. The women's urinal device according to claim 4, wherein the waxed paper provides a smooth waterproof surface to prevent urine from seeping through the generally conical-shaped funnel.

6. The women's urinal device according to claim 4, wherein the waxed paper allows for quick urine flow therethrough the generally conical-shaped funnel.

* * * * *